US012576174B2

(12) United States Patent
Stuck

(10) Patent No.: US 12,576,174 B2
(45) Date of Patent: Mar. 17, 2026

(54) DUAL POLAR AIR AND SURFACE PURIFICATION SYSTEM AND METHOD WITH PASSENGER INTERFACE APPLICATION

(71) Applicant: Ionic Air, LLC, Sharpsburg, GA (US)

(72) Inventor: Eric Edward Stuck, Sharpsburg, GA (US)

( * ) Notice: Subject to any disclaimer, the term of this patent is extended or adjusted under 35 U.S.C. 154(b) by 1175 days.

(21) Appl. No.: 17/515,306

(22) Filed: Oct. 29, 2021

(65) Prior Publication Data

US 2022/0133928 A1 May 5, 2022

Related U.S. Application Data

(60) Provisional application No. 63/108,239, filed on Oct. 30, 2020.

(51) Int. Cl.
*A61L 2/14* (2006.01)
*A61L 9/22* (2006.01)
(52) U.S. Cl.
CPC .................... *A61L 2/14* (2013.01); *A61L 9/22* (2013.01); *A61L 2202/11* (2013.01); *A61L 2202/14* (2013.01); *A61L 2202/25* (2013.01); *A61L 2209/11* (2013.01)
(58) Field of Classification Search
CPC .......... A61L 2/14; A61L 9/22; A61L 2202/11; A61L 2202/14; A61L 2202/25; A61L 2209/11
See application file for complete search history.

(56) References Cited

U.S. PATENT DOCUMENTS

| | | | |
|---|---|---|---|
| 2009/0042502 A1* | 2/2009 | Kim ...................... | B60H 3/0078 |
| | | | 361/231 |
| 2014/0144438 A1* | 5/2014 | Klasek ................. | A61B 5/4812 |
| | | | 128/203.14 |
| 2016/0211654 A1* | 7/2016 | Sekoguchi ............. | H01T 23/00 |
| 2016/0361972 A1 | 12/2016 | Blackley | |
| 2019/0061466 A1 | 2/2019 | MacNeille et al. | |

FOREIGN PATENT DOCUMENTS

WO 2020/055817 A1 3/2020

* cited by examiner

*Primary Examiner* — Maris R Kessel
*Assistant Examiner* — Aham Lee
(74) *Attorney, Agent, or Firm* — Robert M. Ward

(57) ABSTRACT

A dual polar ionization system that introduces ions into passenger transports for the purpose of air and surface purification. The system includes a dual polar ionization generator. The dual polar ionization generator including a control system, a communication system, a positive ion antenna, a negative ion antenna, and a power source. The communication system transmits dual polar ionization output parameters. The system also includes a dual polar ionization user interface for displaying functionality of the dual polar ionization generator including displaying a calculated ion output of the dual polar ionization generator.

6 Claims, 11 Drawing Sheets

100

120

150

130                                                  140

DUAL POLAR AIR AND SURFACE PURIFICATION SYSTEM AND METHOD WITH PASSENGER INTERFACE APPLICATION

BACKGROUND

The present disclosure generally relates to purification systems and methods, and particularly, to ionic purification systems and methods.

Technical Field

Description of the Related Art

Since Covid-19 emerged, people are concerned about traveling on high density passenger vehicles like airplanes, trains, subways, busses, and marine vessels due to risk of infection. These concerns can be at least somewhat alleviated by implementing disinfection and sanitization methods. There is a need to provide both disinfection and sanitization of surfaces, particularly surfaces that are frequently touched, and disinfection and sanitization of the air, particularly in low volume closed spaces.

There is a continuing need in the art for disinfection and sanitization technology that provides a disinfection and sanitization of surfaces and of the air in closed spaces. The present disclosure addresses these and other needs.

BRIEF SUMMARY

In some implementations, the dual polar ionization system introduces ions into passenger transports for the purpose of air and surface purification. The dual polar ionization system includes a dual polar ionization generator having a control system, a communication system, a positive ion antenna, a negative ion antenna, a ion emitter housing, and a power source. The communication system transmits dual polar ionization output parameters to a dual polar ionization user interface. The dual polar ionization user interface displays operational data of the dual polar ionization generator including a calculated ion output of the dual polar ionization generator.

In some embodiments of the system, the ions purify Covid-19, Influenza, the common cold, bacteria, VOCs, smoke, and odors. In another aspect of some embodiments, a soldering sleeve is securely mounted and bonded onto each wire of the positive ion antenna and the negative ion antenna to encapsulate the wires, which results in less than 10 ppb of detectable ozone. In still another aspect of some embodiments, a soldering sleeve is securely mounted and secured onto each wire of the positive ion antenna and the negative ion antenna to encapsulate the wires, which results in less than 5 ppb of detectable ozone. In yet another aspect of some embodiments, the control system in the dual polar ionization generator receives instructions from the dual polar ionization user interface to modify output parameters of the dual polar ionization generator.

In another aspect of some embodiments, the system further includes data bus outputs of the dual polar ionization generator that send a calculated ion output to be interpreted by other electronics systems of a passenger transport. In still another aspect of some embodiments, the system further includes mobile connectivity components that send outputs of the dual polar ionization generator to central operational facilities. In yet another aspect of some embodiments, the calculated ion output data is transmitted via one or more of Bluetooth and Wi-Fi to one or more customers' personal electronic devices, which enables each customer to see that each dual polar ionization generator is activated and functioning properly.

In other implementations, of a dual polar ionization system, the system includes a plurality of dual polar ionization generators and a dual polar ionization user interface. The dual polar ionization generators including a PCB control system, a communication system, a positive ion antenna, a negative ion antenna, an ion emitter housing in which the positive ion antenna and the negative ion antenna are deposed, and a power source. The communication system transmits output parameters from the plurality of dual polar ionization generators. The dual polar ionization user interface displays operational data of the dual polar ionization generators including a calculated ion output of multiple of the plurality of dual polar ionization generators in a passenger transport.

In some embodiments of the system, the ions purify Covid-19, Influenza, the common cold, bacteria, VOCs, smoke, and odors. In another aspect of some embodiments, a soldering sleeve is securely mounted and bonded onto each wire of the positive ion antenna and the negative ion antenna to encapsulate the wires, which results in less than 10 ppb of detectable ozone. In still another aspect of some embodiments, a soldering sleeve is securely mounted and secured onto each wire of the positive ion antenna and the negative ion antenna to encapsulate the wires, which results in less than 5 ppb of detectable ozone. In yet another aspect of some embodiments, the control system in the dual polar ionization generator receives instructions from the dual polar ionization user interface to modify output parameters of the dual polar ionization generator.

In another aspect of some embodiments, the system further includes data bus outputs of the dual polar ionization generator that send a calculated ion output to be interpreted by other electronics systems of a passenger transport. In still another aspect of some embodiments, the system further includes mobile connectivity components that send outputs of the dual polar ionization generator to central operational facilities. In yet another aspect of some embodiments, the calculated ion output data is transmitted via one or more of Bluetooth and Wi-Fi to one or more customers' personal electronic devices, which enables each customer to see that each dual polar ionization generator is activated and functioning properly.

In one or more other implementations, a dual polar ionization system includes a dual polar ionization communication system and a dual polar ionization user interface. The dual polar ionization communication system interfaces with one or more corresponding ion units. The dual polar ionization communication system includes a control system. The dual polar ionization communication system transmits dual polar ionization output parameters from the corresponding ion unit. The one or more corresponding ion units each including an ion emitter. The dual polar ionization user interface displays operational data of the one or more corresponding ion units that is in communication with the dual polar ionization communication system. The dual polar ionization user interface displays a calculated ion output from the one or more corresponding ion units and receives user input to the one or more corresponding ion units.

In some embodiments of the system, the ions purify Covid-19, Influenza, the common cold, bacteria, VOCs, smoke, and odors. In another aspect of some embodiments, a soldering sleeve is securely mounted and bonded onto each wire of the positive ion antenna and the negative ion antenna to encapsulate the wires, which results in less than 10 ppb of detectable ozone. In still another aspect of some embodiments, a soldering sleeve is securely mounted and secured onto each wire of the positive ion antenna and the negative ion antenna to encapsulate the wires, which results in less than 5 ppb of detectable ozone. In yet another aspect of some embodiments, the control system in the dual polar ionization generator receives instructions from the dual polar ionization user interface to modify output parameters of the dual polar ionization generator.

In another aspect of some embodiments, the system further includes data bus outputs of the dual polar ionization generator that send a calculated ion output to be interpreted by other electronics systems of a passenger transport. In still another aspect of some embodiments, the system further includes mobile connectivity components that send outputs of the dual polar ionization generator to central operational facilities. In yet another aspect of some embodiments, the calculated ion output data is transmitted via one or more of Bluetooth and Wi-Fi to one or more customers' personal electronic devices, which enables each customer to see that each dual polar ionization generator is activated and functioning properly.

BRIEF DESCRIPTION OF THE SEVERAL VIEWS OF THE DRAWINGS

In the drawings, identical reference numbers identify similar elements or acts. The sizes and relative positions of elements in the drawings are not necessarily drawn to scale. For example, the shapes of various elements and angles are not necessarily drawn to scale, and some of these elements are arbitrarily enlarged and positioned to improve drawing legibility. Further, the particular shapes of the elements as drawn are not necessarily intended to convey any information regarding the actual shape of the particular elements, and have been solely selected for ease of recognition in the drawings.

DETAILED DESCRIPTION

Figure 1:
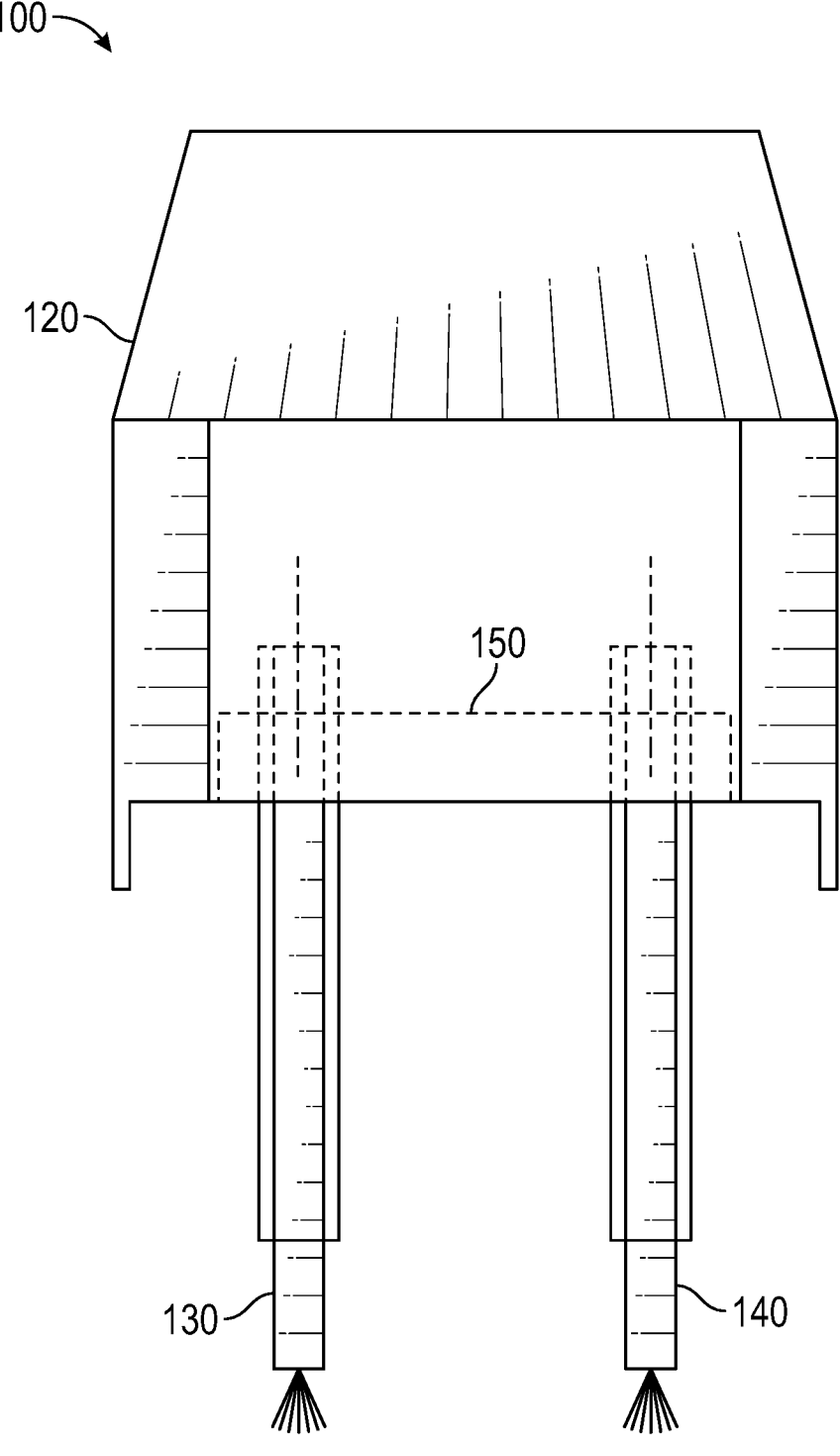
FIG. 1 is a front view of a dual polar air and surface purification system, according to one implementation of the disclosed embodiments.

Persons of ordinary skill in the art will understand that the present disclosure is illustrative only and not in any way limiting. Each of the features and teachings disclosed herein can be utilized separately or in conjunction with other features and teachings to provide a dual polar disinfectant system and method. Representative examples utilizing many of these additional features and teachings, both separately and in combination, are described in further detail with reference to the attached figures. This detailed description is merely intended to teach a person of skill in the art further details for practicing aspects of the present teachings, and is not intended to limit the scope of the claims. Therefore, combinations of features disclosed in the detailed description may not be necessary to practice the teachings in the broadest sense, and are instead taught merely to describe particularly representative examples of the present teachings.

Some portions of the detailed descriptions herein are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities, and are merely convenient labels applied to these quantities. Unless specifically stated otherwise as apparent from the below discussion, it is appreciated that throughout the description, discussions utilizing terms such as "processing," "computing," "calculating," "determining," "displaying," "configuring," or the like, refer to the actions and processes of a computer system, or similar electronic computing device, that manipulate and transform data represented as physical (electronic) quantities within the computer system's registers and memories into other data similarly represented as physical quantities within the computer system memories or registers or other such information storage, transmission or display devices.

Moreover, the various features of the representative examples and the dependent claims may be combined in ways that are not specifically and explicitly enumerated in order to provide additional useful embodiments of the present teachings. It is also expressly noted that all value ranges or indications of groups of entities disclose every possible intermediate value or intermediate entity for the purpose of original disclosure, as well as for the purpose of restricting the claimed subject matter. It is also expressly noted that the dimensions and the shapes of the components shown in the figures are designed to help to understand how the present teachings are practiced, but not intended to limit the dimensions and the shapes shown in the examples.

Unless the context requires otherwise, throughout the specification and claims which follow, the word "comprise" and variations thereof, such as "comprises" and "comprising," are to be construed in an open, inclusive sense, that is, as "including, but not limited to." Reference throughout this specification to "one implementation" or "an implementation" means that a particular feature, structures, or characteristics may be combined in any suitable manner in one or more implementations.

As used in this specification and the appended claims, the singular forms "a," "an," and "the" include plural referents unless the content clearly dictates otherwise. It should also be noted that the term "or" is generally employed in its broadest sense, that is, as meaning "and/or" unless the content clearly dictates otherwise. The headings and Abstract of the Disclosure provided herein are for convenience only and do not interpret the scope or meaning of the implementations.

FIGS. 1, 2, 3A, and 3B show a dual polar air and surface purification system and method 100, according to one implementation of the disclosed embodiments. In some embodiments, the dual polar air and surface purification system and method 100 introduces a sufficient density of positive and negative ions into the passenger compartments on vehicles and vessels to be over 99% effective in neutralizing Covid-19. The dual polar air and surface purification system and method 100 also neutralizes and kills many other viruses such as Influenza, the common cold, bacteria, volatile organic compounds (VOCs), smoke, and odors. While bi-polar ionization has been previously used in some situations, its high cost, and unwanted ozone production, and lack of any visual and/or touch interface has limited its adoption. The technological improvements of the dual polar air and surface purification system and method 100 overcome these previous problems with bi-polar ionization implementation.

Figure 2:
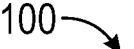
FIG. 2 is a back view of a dual polar air and surface purification system, according to one implementation of the disclosed embodiments.
Figure 2:
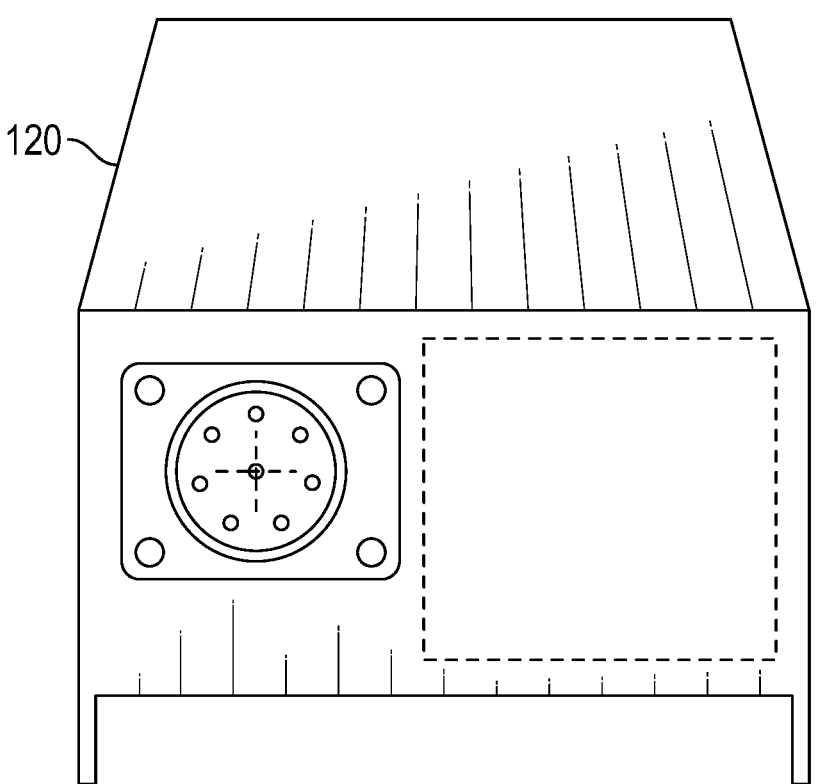
Figure 3A:
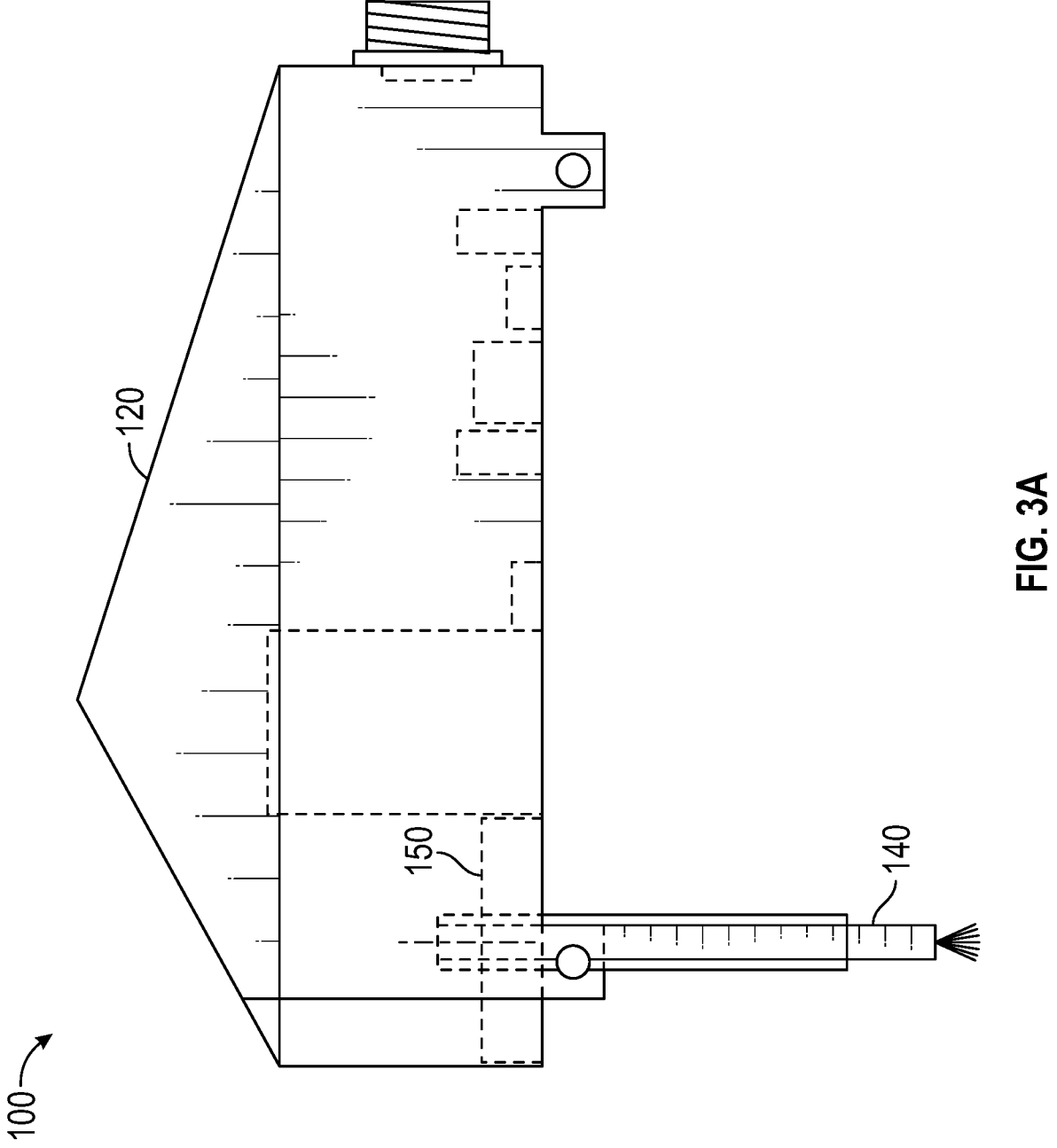
FIG. 3A is a side view of a dual polar air and surface purification system, according to one implementation of the disclosed embodiments.
Figure 3B:
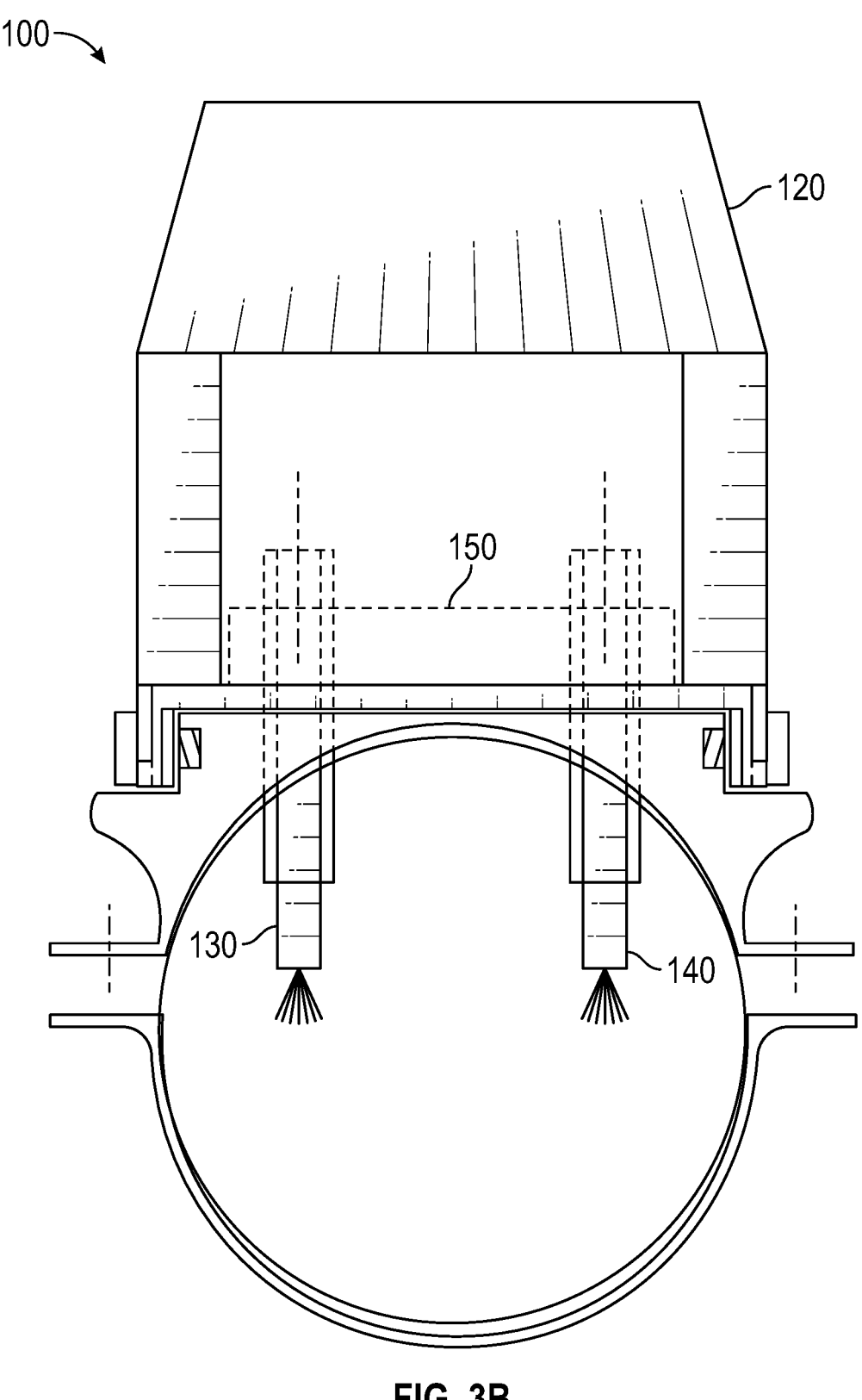
FIG. 3B is a back view of a dual polar air and surface purification system mounted on a ventilation duct with the dual polar antennas extending into the ventilation duct, according to one implementation of the disclosed embodiments.

FIG. 1 is a front view of a dual polar air and surface purification system 100. The dual polar air and surface purification system 100 includes a housing 120, a positive ion antenna 130, and a negative ion antenna 140, and a combined ion emitter housing 150. The positive ion antenna 130 and the negative ion antenna 140 each include a wire. The combined ion emitter housing 150 is configured to receive the positive ion antenna 130 and a negative ion antenna 140. FIG. 2 is a back view of a dual polar air and surface purification system 100. FIG. 3A is a side view of a dual polar air and surface purification system 100. FIG. 3B is a back view of a dual polar air and surface purification system 100 mounted on a ventilation duct with the dual polar antennas 130 and 140 extending into the ventilation duct.

Figure 4A:
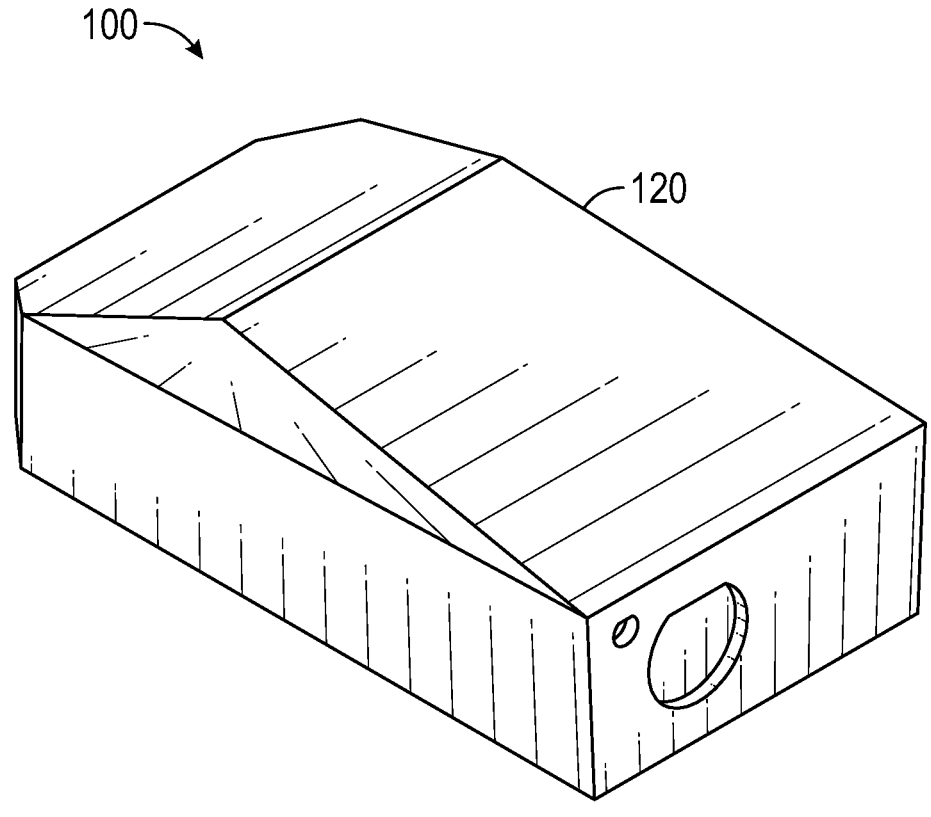
FIG. 4A is a back perspective of the dual polar air and surface purification system, according to one implementation of the disclosed embodiments.
Figure 4B:
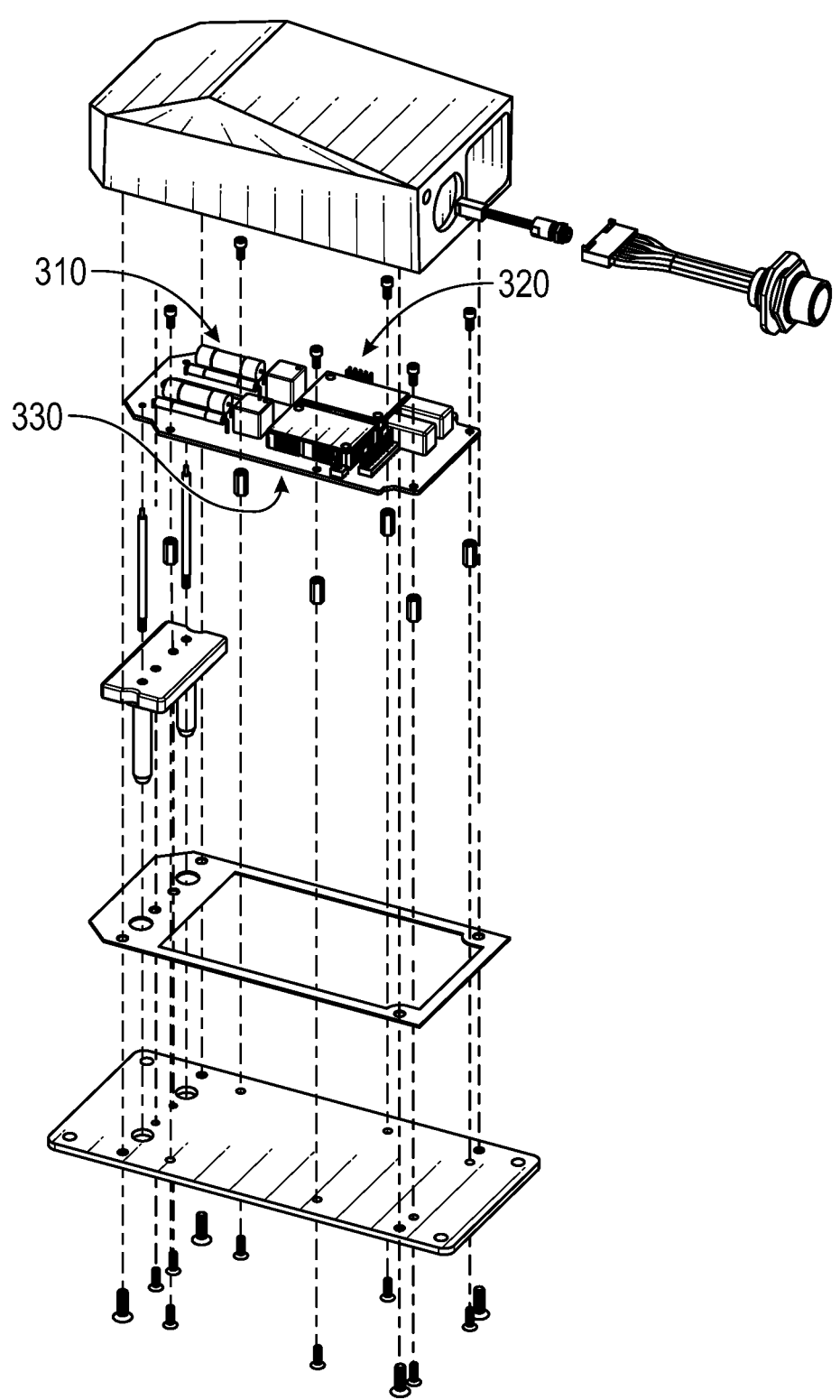
FIG. 4B is an exploded view of the dual polar air and surface purification system with the housing lifted to expose the printed circuit board with the power source, control system, and communication system, according to one implementation of the disclosed embodiments.

Referring now to FIG. 4A, FIG. 4A shows a back perspective view of the dual polar air and surface purification system 100 with the unique angles of the housing. In FIG. 4B, in exploded view of the dual polar air and surface purification system 100 is shown with the housing 120 lifted to expose the power source 310, the control system 320, and the communication system 330. While various components of the dual polar air and surface purification system 100 are shown as individual components in the embodiment of FIG. 4B, in other embodiments, some of these components are combined into fewer components.

Figure 4C:
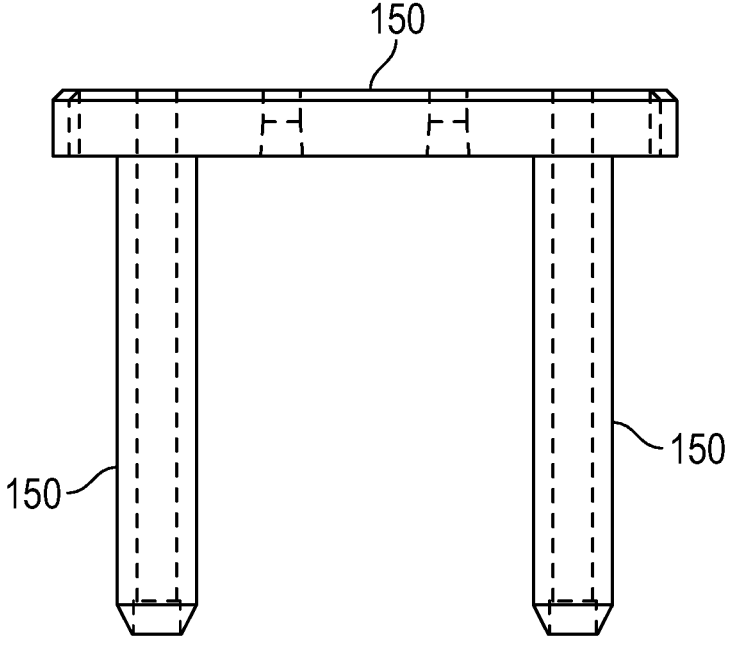
FIG. 4C is an end view of the positive ion antenna and negative ion antenna of the dual polar air and surface purification system, according to one implementation of the disclosed embodiments.

Referring now to FIG. 4C, an embodiment of the combined ion emitter housing 150 is shown that includes a base plate and two arm housings as single formed unit. In some embodiments of the dual polar air and surface purification system 100, the two arm housing of the combined ion emitter housing 150 are configured to receive the positive ion antenna 130 and the negative ion antenna 140. In other embodiments of the dual polar air and surface purification system 100, ion emitter housing 150 may be comprises of multiple components.

Figure 4D:
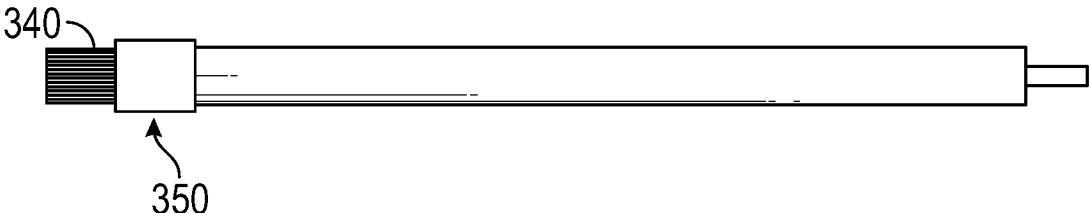
FIG. 4D is a side view of an ion antenna of the dual polar air and surface purification system with a soldering sleeve securely mounted and bonded onto the wire of the ion antenna, according to one implementation of the disclosed embodiments.

Referring now to FIG. 4D, an ion antenna of the dual polar air and surface purification system 100 is shown with a soldering sleeve 350 securely mounted and bonded onto the wire of an antenna. In some embodiments, the soldering sleeve 350 encapsulates the wire of an ion antenna. In some embodiments, the Ionic Air Care proprietary ion emitter assembly uses a soldering sleeve 350 with very high electrical and mechanical bonding between the wire and the carbon graphite filament bundle 340. Some preferred embodiments of the ion antenna of the dual polar air and surface purification system 100 exhibit less than 10 ppb of Ozone production during operation of ionization unit. Other more preferred embodiments of the ion antenna 130 or 140 of the dual polar air and surface purification system 100 exhibit less than 5 ppb of Ozone production during operation of ionization unit. Intertek UL 867 Ozone production testing may be used to pinpoint Ozone generation. Notably, a dual polar air and surface purification system 100 that exhibits less than 5 ppb of Ozone production may be certified as Ozone free.

This technique of employing a soldering sleeve 350 that is securely mounted and bonded onto the wire of an ion antenna is a technological improvement over prior devices that have employed "horse collar" bonding (or other techniques), which do not provide the encapsulation of the wires of the ion antennas in the dual polar air and surface purification system 100. Such prior devices without this encapsulation of the wires of the ion antennas 130 and 140 produce much higher levels of detectable Ozone (e.g., 15 ppb, 40, or more), which is highly undesirable for health reasons.

Figure 4E:
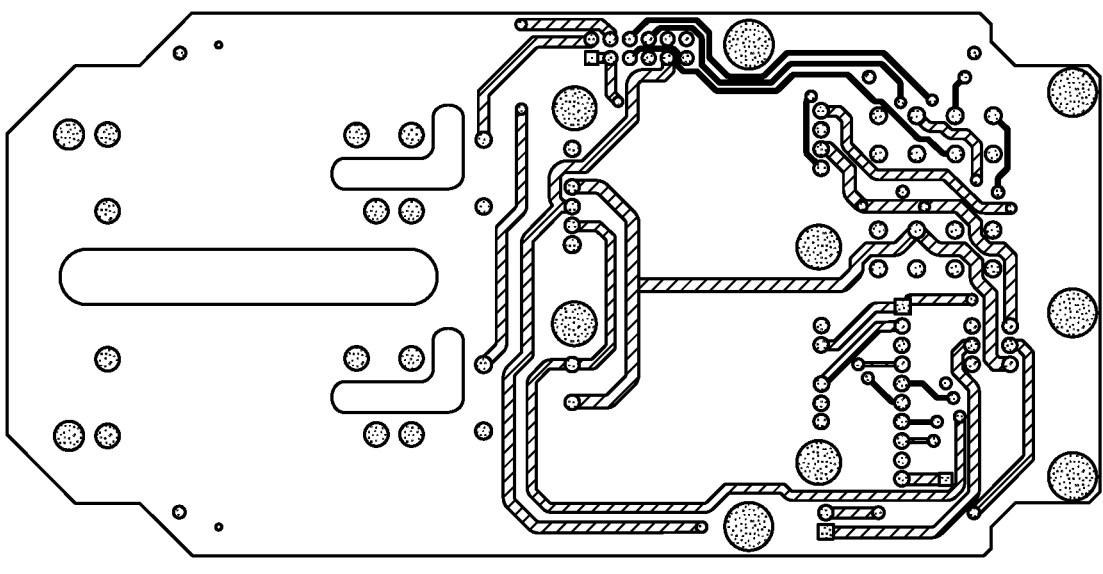
FIG. 4E is a top view of one layer of the printed circuit board of the dual polar air and surface purification system, according to one implementation of the disclosed embodiments.
Figure 4F:
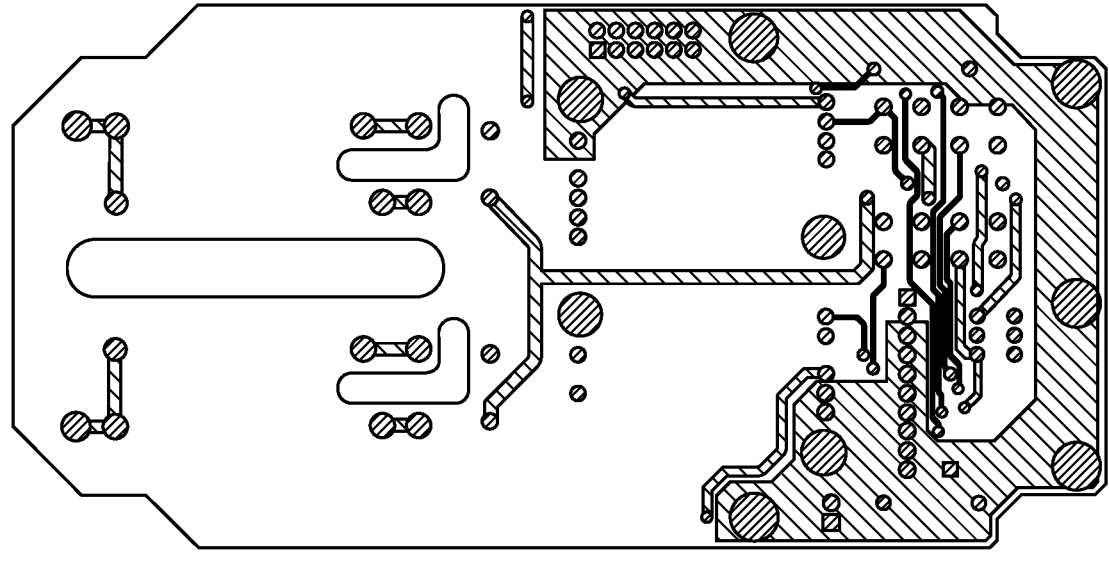
FIG. 4F is a top view of another layer of the printed circuit board of the dual polar air and surface purification system, according to one implementation of the disclosed embodiments.
Figure 4G:
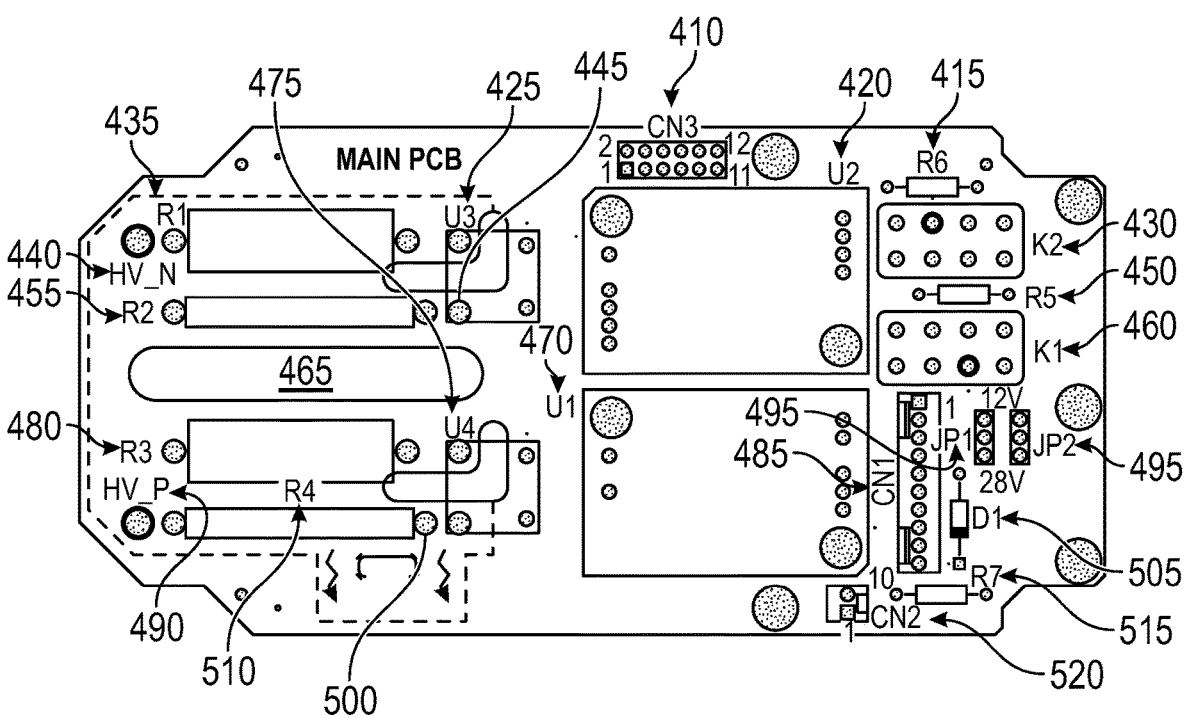
FIG. 4G is a top view of still another layer of the printed circuit board of the dual polar air and surface purification system, according to one implementation of the disclosed embodiments.

Referring now to FIGS. 4E, 4F, and 4G, one embodiment of the PCB (printed circuit board, e.g., control system) of the dual polar air and surface purification system 100 is shown in detail. Referring specifically to FIG. 4G, reference components 410-520 of one or more embodiments of the printed circuit board in the dual polar air and surface purification system 100 are shown.

Reference number 410 shows component CN3, which is an A12 pin PCB mounted data communications smart data card expansion and remote ionization mode control connector. Reference number 415 shows component R6, which is a MIL-SPEC PCB mounted U2 trim down resistor for decreased ionization level. Reference number 420 shows component U2, which is a MIL-SPEC PCB mounted DC-DC voltage converter. Reference number 425 shows component U3, which is a MIL-SPEC PCB mounted negative high voltage power supply. Reference number 430 shows component K2, which is a MIL-SPEC PCB mounted dual level ionization mode control relay. Reference number 435 shows component R1, which is an MIL-SPEC PCB mounted short protection output resistor.

Reference number 440 shows component HV_N, which is a PCB through hole and electrical connection to negative high voltage output resistor network. Reference number 445 shows a Physical channel cutout in PCB for negative high voltage-high altitude short protection. Reference number 450 shows component R5, which is a MIL-SPEC PCB mounted U2 trim up resistor for increased ionization level.

Reference number 455 shows component R2, which is a MIL-SPEC PCB mounted output voltage development resistor.

Reference number 460 shows component K1, which is a MIL-SPEC PCB mounted in cabin annunciation control relay. Reference number 465 shows a Physical channel cutout in PCB for negative and positive high voltage separation.

Reference number 470 shows component U1, which is a MIL-SPEC PCB mounted Input power filter. Reference number 475 shows component U4, which is a MIL-SPEC PCB mounted positive high voltage power supply. Reference number 480 shows component R3, which is a MIL-SPEC PCB mounted short protection output resistor. Reference number 485 shows component CN1, which is a 10 pin PCB mounted main unit connector. Reference number 490 shows component HV_P, which is a PCB through hole and electrical connection to positive high voltage output resistor network. Reference number 495 shows components, JP1 & JP2 through hole jumper options for cover mounted LED operating voltage of 12 VDC or 28 VDC.

Reference number 500 shows a Physical channel cutout in PCB for positive high voltage-high altitude short protection. Reference number 505 shows component D1, which is a MIL-SPEC PCB mounted trim up ionization level—aircraft weight on wheels (WOW) signal isolation diode. Reference number 510 shows component R4, which is a MIL-SPEC PCB mounted output voltage development resistor. Reference number 515 shows component R7, which is a MIL-SPEC PCB mounted cover mounted Light Emitting Diode (LED) load resistor. Reference number 520 shows component CN2, which is a 2 pin PCB mounted cover mounted LED connector.

Figure 5:
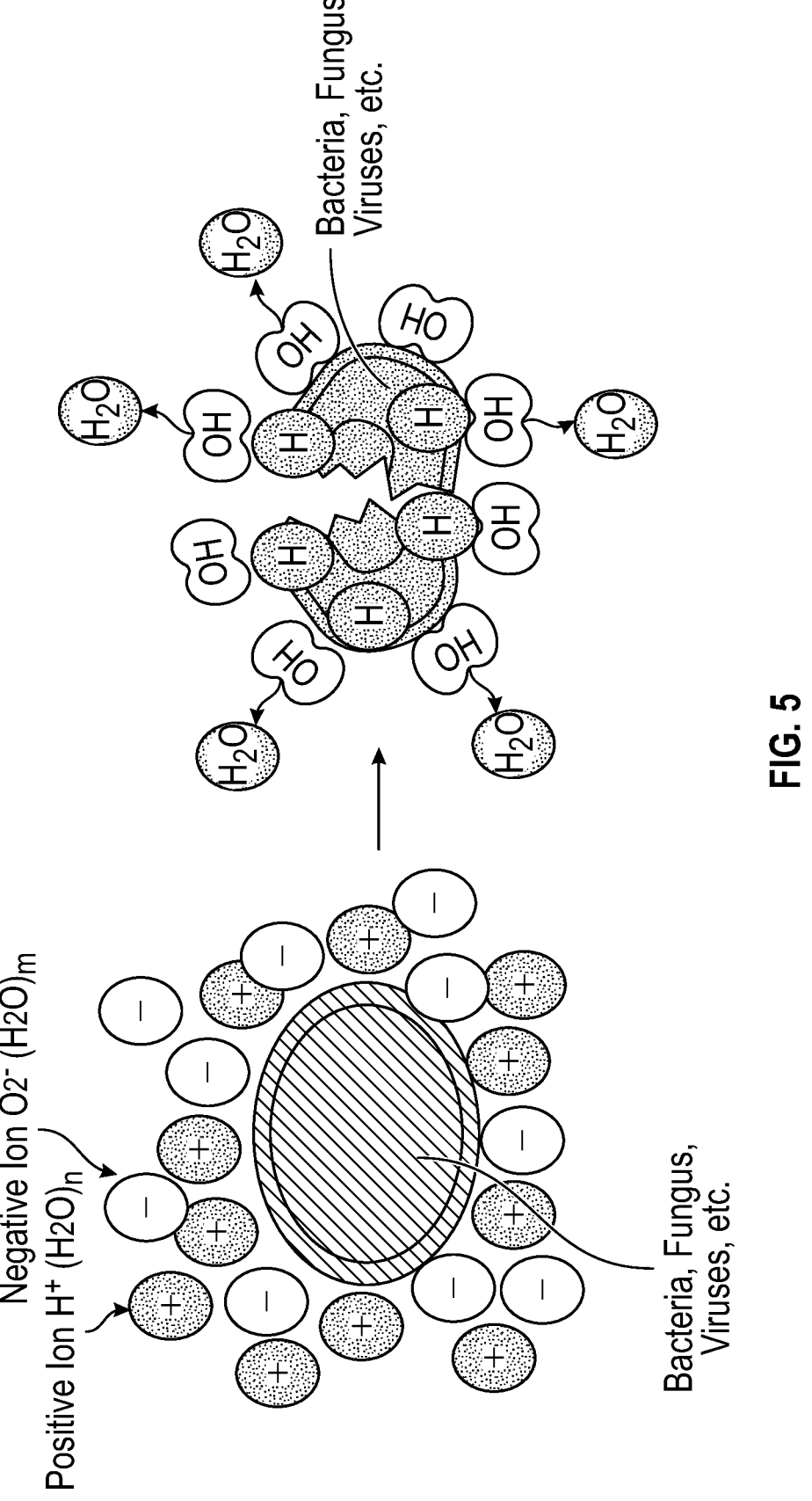
FIG. 5 is an illustration of dual polar ion particles (i.e., positive and negative ions) neutralizing a virus.

In some embodiments, the dual polar air and surface purification system and method 100 includes a passenger interface application for high density passenger vehicles and vessels that monitors and displays the output of the ion generation units. In other embodiments of the dual polar air and surface purification system and method 100, at least some of the passenger interface applications enable output control of the ion generation units, as well as the monitoring and displaying of the output of the ion generation units. The distribution of these applications would typically be limited to those with the proper authorization to be able to control the ion generation units. The ion generation units (hereafter called "Ion Units") have the appropriate input voltage for various aircraft, Hyperloop pods, trains, subway cars, busses, and marine vessels and deployed with enough units to attain the level of ionization needed to effectively neutralize Covid-19, as well as other viruses, bacteria, Volatile Organic Compounds (VOCs), smoke, and odors, as shown in FIG. 5.

Additionally, in some embodiments of the dual polar air and surface purification system and method 100, each ion unit is equipped with one or more of a variety of Bluetooth and Wi-Fi devices, which will transmit the calculated number of positive and negative ions currently being produced, along with the total ion output to a passenger's (hereafter called "User or Users") personal electronic device(s) (hereafter called "PED or PEDs") for personal awareness, edification, and safety.

In one or more embodiments of the dual polar air and surface purification system and method 100, the Ion Units are equipped to measure the voltage level at the output of the high voltage power supply, which is directly connected to the ion generation emitters and calculate in real-time the ion output of the Ion Units. The calculated ion output data is transmitted via one or more of Bluetooth and Wi-Fi to the customer's PED(s) via an installed Android Ionic Air App, iOS Ionic Air App or HTMLS web browser page (hereafter called "Ionic Air App").

In the dual polar air and surface purification system and method 100, the data is interpreted by the User's Ionic Air App, which enables each customer to see that each ion unit is on and functioning. The customer's Ionic Air App also displays the current calculated level of ion generation and other parameters including, but not limited to; Ion Unit, input voltage, output voltage, operating temperature, Bluetooth and Wi-Fi device's state and operational condition, and the like.

In the Bluetooth-only versions of the Ion Units in the dual polar air and surface purification system and method 100, Users see all Ion Units within signal strength range on the User's Ionic Air App. The User's Ionic Air App also dynamically displays the Ion Units in range as the User moves within the User's Transport.

In Bluetooth and Wi-Fi versions of the Ion Units in the dual polar air and surface purification system and method 100, Users see all Ion Units within Bluetooth signal strength range on their Ionic Air App. The User's Ionic Air App also dynamically displays the Ion Units in range as the User moves within the User's Transport. Additionally, the User has the ability to see all units installed on a given User's Transport while onboard via Wi-Fi connectivity using the Ionic Air App. With Wi-Fi enabled units, the Ion Unit's data may also be displayed on other displays within the Transport using the Ionic Air App. In additional or alternatively to display on the Ionic Air App, this visualization data may also be displayed on seat back monitors or other display devices.

In other embodiments, the dual polar air and surface purification system 100 also includes a smart data card. In some such embodiments, the smart data card of the dual polar air and surface purification system 100 is a physical three wire, one-way data output of the same information described above that is sent via Bluetooth or WiFi. In some embodiments that are civil aviation based, the protocols may be ARINC 429 or 664 data protocols. In other embodiments for military or other applications, Mil 1553 or other data formats may be implemented. These protocols are presented by way of example only, and not by way of limitation. In another aspect of some embodiments, the ionization unit has three pins dedicated for this purpose on CN3, CN1, and the main P1 external connector. In some such embodiments, the three wires consist of a data+, data−, and signal shield.

In various embodiments of the dual polar air and surface purification system and method 100, compatible Ion Units have various data bus outputs for example, but not limited to RS-232, ARINC 429, ARINC 629, ARINC 664, Micro AFDX, IEEE 802.11 Ethernet, MIL STD 1553, and other types of data busses. The data busses contain all parameters available via Wi-Fi along with any additional available parameters requested by the specific market segment.

US 12,576,174 B2

Figure 6:
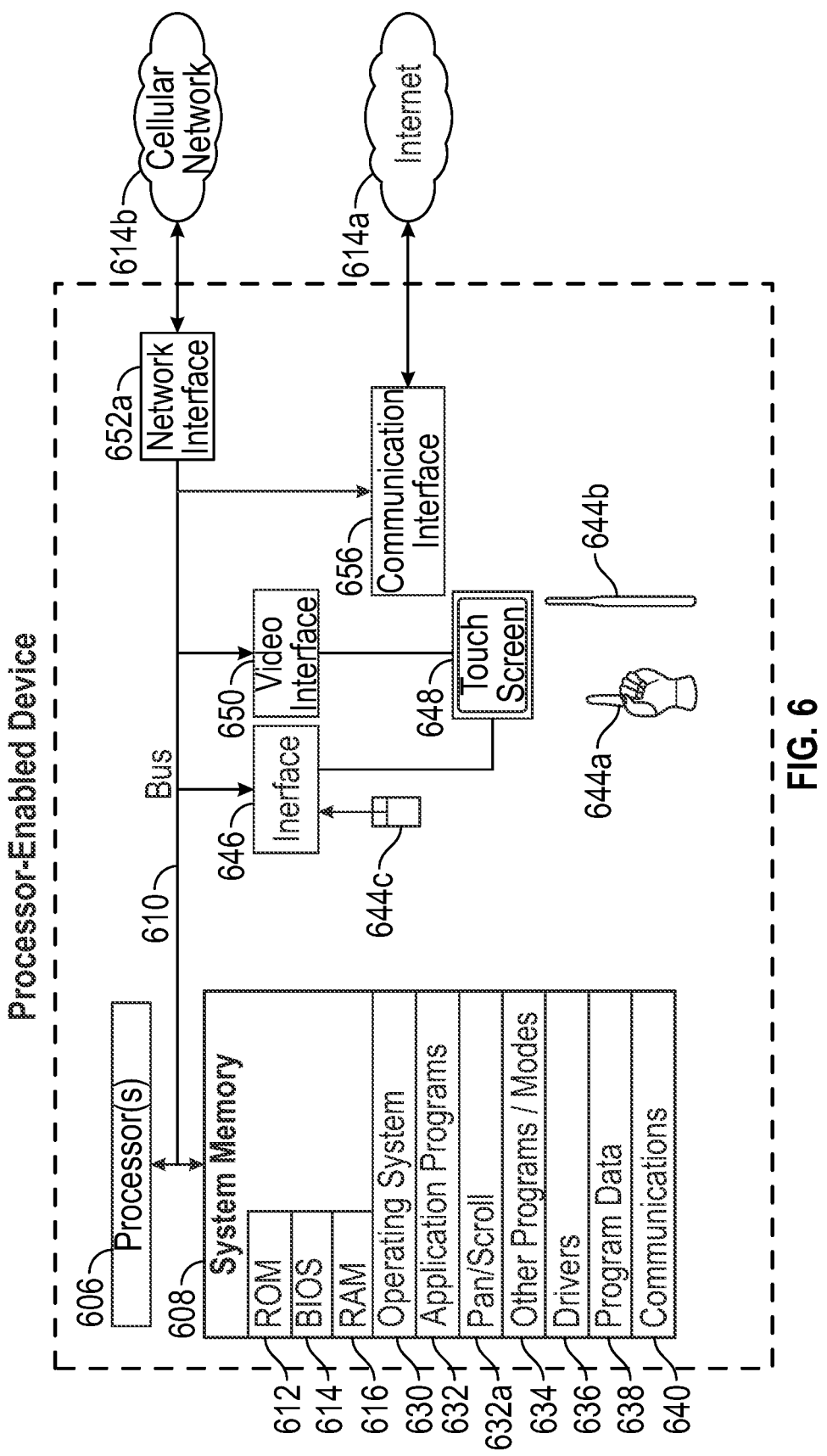
FIG. 6 is a block diagram of an example processor-based device used to implement one or more of the dual polar air and surface purification systems described herein.

For use in conjunction with the dual polar disinfectant system 100, FIG. 6 shows a processor-based device suitable for implementing the dual polar disinfectant system 100, as well as the processor-based mobile devices that support the applications used in conjunction with the system. Although not required, some portion of the implementations will be described in the general context of processor-executable instructions or logic, such as program application modules, objects, or macros being executed by one or more processors. Those skilled in the relevant art will appreciate that the described implementations, as well as other implementations, can be practiced with various processor-based system configurations, including handheld devices, such as smartphones and tablet computers, wearable devices, multiprocessor systems, microprocessor-based or programmable consumer electronics, personal computers ("PCs"), network PCs, minicomputers, mainframe computers, and the like.

In the dual polar disinfectant system 100, the processor-based device may, for example, take the form of a smartphone or wearable smart glasses, which includes one or more processors 606, a system memory 608 and a system bus 610 that couples various system components including the system memory 608 to the processor(s) 606. The processor-based device will, at times, be referred to in the singular herein, but this is not intended to limit the implementations to a single system, since in certain implementations, there will be more than one system or other networked computing device involved. Non-limiting examples of commercially available systems include, but are not limited to, ARM processors from a variety of manufactures, Core microprocessors from Intel Corporation, U.S.A., PowerPC microprocessor from IBM, Sparc microprocessors from Sun Microsystems, Inc., PA-RISC series microprocessors from Hewlett-Packard Company, and 68xxx series microprocessors from Motorola Corporation.

The processor(s) 606 in the processor-based devices of the dual polar disinfectant system 100 may be any logic processing unit, such as one or more central processing units (CPUs), microprocessors, digital signal processors (DSPs), application-specific integrated circuits (ASICs), field programmable gate arrays (FPGAs), and the like. Unless described otherwise, the construction and operation of the various blocks shown in FIG. 6 are of conventional design. As a result, such blocks need not be described in further detail herein, as they will be understood by those skilled in the relevant art.

The system bus 610 in the processor-based devices of the dual polar disinfectant system 100 can employ any known bus structures or architectures, including a memory bus with memory controller, a peripheral bus, and a local bus. The system memory 608 includes read-only memory ("ROM") 612 and random access memory ("RAM") 614. A basic input/output system ("BIOS") 616, which can form part of the ROM 612, contains basic routines that help transfer information between elements within processor-based device, such as during start-up. Some implementations may employ separate buses for data, instructions and power.

The processor-based device of the dual polar disinfectant system 100 may also include one or more solid state memories; for instance, a Flash memory or solid state drive (SSD), which provides nonvolatile storage of computer-readable instructions, data structures, program modules and other data for the processor-based device. Although not depicted, the processor-based device can employ other non-transitory computer- or processor-readable media, for example, a hard disk drive, an optical disk drive, or a memory card media drive.

Program modules in the processor-based devices of the dual polar disinfectant system 100 can be stored in the system memory 608, such as an operating system 630, one or more application programs 632, other programs or modules 634, drivers 636 and program data 638.

The application programs 632 may, for example, include panning/scrolling 632*a*. Such panning/scrolling logic may include, but is not limited to, logic that determines when and/or where a pointer (e.g., finger, stylus, cursor) enters a user interface element that includes a region having a central portion and at least one margin. Such panning/scrolling logic may include, but is not limited to, logic that determines a direction and a rate at which at least one element of the user interface element should appear to move, and causes updating of a display to cause the at least one element to appear to move in the determined direction at the determined rate. The panning/scrolling logic 632*a* may, for example, be stored as one or more executable instructions. The panning/scrolling logic 632*a* may include processor and/or machine executable logic or instructions to generate user interface objects using data that characterizes movement of a pointer, for example, data from a touch-sensitive display or from a computer mouse or trackball, or other user interface device.

The system memory 608 in the processor-based devices of the dual polar disinfectant system 100 may also include communications programs 640, for example, a server and/or a Web client or browser for permitting the processor-based device to access and exchange data with other systems such as user computing systems, Web sites on the Internet, corporate intranets, or other networks as described below. The communications program 640 in the depicted implementation is markup language based, such as Hypertext Markup Language (HTML), Extensible Markup Language (XML) or Wireless Markup Language (WML), and operates with markup languages that use syntactically delimited characters added to the data of a document to represent the structure of the document. A number of servers and/or Web clients or browsers are commercially available such as those from Mozilla Corporation of California and Microsoft of Washington.

While shown in FIG. 6 as being stored in the system memory 608, operating system 630, application programs 632, other programs/modules 634, drivers 636, program data 638 and server and/or browser can be stored on any other of a large variety of nontransitory processor-readable media (e.g., hard disk drive, optical disk drive, SSD and/or flash memory).

A user of a processor-based device in the dual polar disinfectant system 100 can enter commands and information via a pointer, for example, through input devices such as a touch screen 648 via a finger 644*a*, stylus 644*b*, or via a computer mouse or trackball 644*c* which controls a cursor. Other input devices can include a microphone, joystick, game pad, tablet, scanner, biometric scanning device, and the like. These and other input devices (i.e., "I/O devices") are connected to the processor(s) 606 through an interface 646 such as a touch-screen controller and/or a universal serial bus ("USB") interface that couples user input to the system bus 610, although other interfaces such as a parallel port, a game port or a wireless interface or a serial port may be used. The touch screen 648 can be coupled to the system bus 610 via a video interface 650, such as a video adapter to receive image data or image information for display via the touch screen 648. Although not shown, the processor-based device can include other output devices, such as speakers, vibrator, haptic actuator or haptic engine, and the like.

The processor-based devices of the dual polar disinfectant system 100 operate in a networked environment using one or more of the logical connections to communicate with one or more remote computers, servers and/or devices via one or more communications channels, for example, one or more networks 614a, 614b. These logical connections may facilitate any known method of permitting computers to communicate, such as through one or more LANs and/or WANs, such as the Internet, and/or cellular communications networks. Such networking environments are well known in wired and wireless enterprise-wide computer networks, intranets, extranets, the Internet, and other types of communication networks including telecommunications networks, cellular networks, paging networks, and other mobile networks.

When used in a networking environment, the processor-based devices of the dual polar disinfectant system 100 may include one or more network, wired or wireless communications interfaces 652a, 656 (e.g., network interface controllers, cellular radios, WI-FI radios, Bluetooth radios) for establishing communications over the network, for instance, the Internet 614a or cellular network 614b.

In a networked environment, program modules, application programs, or data, or portions thereof, can be stored in a server computing system (not shown). Those skilled in the relevant art will recognize that the network connections shown in FIG. 6 are only some examples of ways of establishing communications between computers, and other connections may be used, including wirelessly.

For convenience, the processor(s) 606, system memory 608, and network and communications interfaces 652a, 656 are illustrated as communicably coupled to each other via the system bus 610, thereby providing connectivity between the above-described components. In alternative implementations of the processor-based device, the above-described components may be communicably coupled in a different manner than illustrated in FIG. 6. For example, one or more of the above-described components may be directly coupled to other components, or may be coupled to each other, via intermediary components (not shown). In some implementations, system bus 610 is omitted, and the components are coupled directly to each other using suitable connections.

Throughout this specification and the appended claims the term "communicative" as in "communicative pathway," "communicative coupling," and in variants such as "communicatively coupled," is generally used to refer to any engineered arrangement for transferring and/or exchanging information. Exemplary communicative pathways include, but are not limited to, electrically conductive pathways (e.g., electrically conductive wires, electrically conductive traces), magnetic pathways (e.g., magnetic media), one or more communicative link(s) through one or more wireless communication protocol(s), and/or optical pathways (e.g., optical fiber), and exemplary communicative couplings include, but are not limited to, electrical couplings, magnetic couplings, wireless couplings, and/or optical couplings.

Throughout this specification and the appended claims, infinitive verb forms are often used. Examples include, without limitation: "to detect," "to provide," "to transmit," "to communicate," "to process," "to route," and the like. Unless the specific context requires otherwise, such infinitive verb forms are used in an open, inclusive sense, that is as "to, at least, detect," "to, at least, provide," "to, at least, transmit," and so on.

The above description of illustrated implementations, including what is described in the Abstract, is not intended to be exhaustive or to limit the implementations to the precise forms disclosed. Although specific implementations of and examples are described herein for illustrative purposes, various equivalent modifications can be made without departing from the spirit and scope of the disclosure, as will be recognized by those skilled in the relevant art. The teachings provided herein of the various implementations can be applied to other portable and/or wearable electronic devices, not necessarily the exemplary wearable electronic devices generally described above.

For instance, the foregoing detailed description has set forth various implementations of the devices and/or processes via the use of block diagrams, schematics, and examples. Insofar as such block diagrams, schematics, and examples contain one or more functions and/or operations, it will be understood by those skilled in the art that each function and/or operation within such block diagrams, flowcharts, or examples can be implemented, individually and/or collectively, by a wide range of hardware, software, firmware, or virtually any combination thereof. In one implementation, the present subject matter may be implemented via Application Specific Integrated Circuits (ASICs). However, those skilled in the art will recognize that the implementations disclosed herein, in whole or in part, can be equivalently implemented in standard integrated circuits, as one or more computer programs executed by one or more computers (e.g., as one or more programs running on one or more computer systems), as one or more programs executed by one or more controllers (e.g., microcontrollers) as one or more programs executed by one or more processors (e.g., microprocessors, central processing units, graphical processing units), as firmware, or as virtually any combination thereof, and that designing the circuitry and/or writing the code for the software and or firmware would be well within the skill of one of ordinary skill in the art in light of the teachings of this disclosure.

When logic is implemented as software and stored in memory, logic or information can be stored on any processor-readable medium for use by or in connection with any processor-related system or method. In the context of this disclosure, a memory is a processor-readable medium that is an electronic, magnetic, optical, or other physical device or means that contains or stores a computer and/or processor program. Logic and/or the information can be embodied in any processor-readable medium for use by or in connection with an instruction execution system, apparatus, or device, such as a computer-based system, processor-containing system, or other system that can fetch the instructions from the instruction execution system, apparatus, or device and execute the instructions associated with logic and/or information.

In the context of this specification, a "non-transitory processor-readable medium" can be any element that can store the program associated with logic and/or information for use by or in connection with the instruction execution system, apparatus, and/or device. The processor-readable medium can be, for example, but is not limited to, an electronic, magnetic, optical, electromagnetic, infrared, or semiconductor system, apparatus or device. More specific examples (a non-exhaustive list) of the computer readable medium would include the following: a portable computer diskette (magnetic, compact flash card, secure digital, or the like), a random access memory (RAM), a read-only memory (ROM), an erasable programmable read-only memory (EPROM, EEPROM, or Flash memory), a portable compact disc read-only memory (CDROM), digital tape, and other non-transitory media.

The various implementations described above can be combined to provide further implementations. To the extent that they are not inconsistent with the specific teachings and definitions herein, all of the U.S. patents, U.S. patent application publications, U.S. patent applications, foreign patents, foreign patent applications and non-patent publications referred to in this specification and/or listed in the Application Data Sheet, are incorporated herein by reference, in their entirety. Aspects of the implementations can be modified, if necessary, to employ systems, circuits and concepts of the various patents, applications and publications to provide yet further implementations.

These and other changes can be made to the implementations in light of the above-detailed description. In general, in the following claims, the terms used should not be construed to limit the claims to the specific implementations disclosed in the specification and the claims, but should be construed to include all possible implementations along with the full scope of equivalents to which such claims are entitled. Accordingly, the claims are not limited by the disclosure.

The invention claimed is:

1. A dual polar ionization system that with material avoidance of ozone generation introduces ions into passenger transport spaces of high-density passenger vehicles, such as airplanes, trains, subways, busses, and marine vessels, to provide purified air for beneficial breathing by passengers, the system comprising:

a dual polar ionization generator disposed within the passenger transport space of the high-density passenger vehicle, the dual polar ionization generator including a control system, a communication system, a positive ion antenna comprising a discharge carbon bundle connected at an interface thereof to an electrically-conductive wire having appropriate input voltage for the passenger transport space of the high-density passenger vehicle, a negative ion antenna comprising a discharge carbon bundle connected at an interface thereof to an electrically-conductive wire having appropriate input voltage for the passenger transport space of the high-density passenger vehicle, an ion emitter housing, and a power source, wherein the communication system transmits dual polar ionization output parameters; and a dual polar ionization user interface for displaying functionality of the dual polar ionization generator including displaying a calculated ion output of the dual polar ionization generator; and a soldering sleeve securely encapsulating the interface connection between the discharge carbon bundle and the corresponding electrically-conductive wire of each of the positive ion antenna and the negative ion antenna, thereby to suppress generation of ozone production within the high density passenger space.

2. The system of claim 1, wherein the ions purify Covid-19, Influenza, the common cold, bacteria, VOCs, smoke, and odors.

3. The system of claim 1, further comprising: mobile connectivity components that send outputs of the dual polar ionization generator to central operational facilities.

4. The system of claim 1, wherein the calculated ion output data is transmitted via wireless communication to one or more customers' personal electronic devices, which enables each customer to see that each dual polar ionization generator is activated and functioning properly.

5. The system of claim 1, wherein the control system in the dual polar ionization generator receives instructions from the dual polar ionization user interface to modify output parameters of the dual polar ionization generator.

6. The system of claim 1, further comprising: a dual polar ionization generator that outputs data using a data bus to send a calculated ion output to be interpreted by other electronics systems of a passenger transport.

* * * * *